United States Patent
De Lacharriere et al.

(10) Patent No.: US 8,088,399 B2
(45) Date of Patent: Jan. 3, 2012

(54) USE OF ACTIVE PRINCIPLES WHICH ARE CAPABLE OF ENHANCING THE CONTENT OF CERAMIDES, AS PROTECTIVE AGENT FOR DELICATE LIPS

(75) Inventors: Olivier De Lacharriere, Paris (FR); Odette Jammayrac, Boulogne (FR); Véronique Burnier, Draveil (FR); Boudiaf Boussouira, Paris (FR)

(73) Assignee: L'Oreal, Paris (FR)

( * ) Notice: Subject to any disclaimer, the term of this patent is extended or adjusted under 35 U.S.C. 154(b) by 8 days.

(21) Appl. No.: 12/007,669

(22) Filed: Jan. 14, 2008

(65) Prior Publication Data

US 2008/0213323 A1 Sep. 4, 2008

Related U.S. Application Data

(60) Provisional application No. 60/902,857, filed on Feb. 23, 2007.

(30) Foreign Application Priority Data

Jan. 12, 2007 (FR) ...................................... 07 52658
Jul. 16, 2007 (FR) ...................................... 07 56522

(51) Int. Cl.
*A61K 8/02* (2006.01)
*A01N 43/08* (2006.01)

(52) U.S. Cl. ........................................ 424/401; 514/474
(58) Field of Classification Search ................... 424/401
See application file for complete search history.

(56) References Cited

U.S. PATENT DOCUMENTS

| | | | |
|---|---|---|---|
| 5,589,178 A | 12/1996 | Aubert et al. | |
| 5,665,778 A | 9/1997 | Semeria et al. | |
| 5,776,480 A | 7/1998 | Candau et al. | |
| 5,798,108 A * | 8/1998 | Nadaud et al. | 424/401 |
| 5,874,069 A | 2/1999 | Mendolia et al. | |
| 5,919,441 A | 7/1999 | Mendolia et al. | |
| 5,981,680 A | 11/1999 | Petroff et al. | |
| 6,051,216 A | 4/2000 | Barr et al. | |
| 6,099,826 A * | 8/2000 | Ramin | 424/61 |
| 6,183,761 B1 * | 2/2001 | Bissett et al. | 424/401 |
| 2003/0095936 A1 | 5/2003 | Light | |
| 2004/0092482 A1 | 5/2004 | Gupta | |
| 2007/0065392 A1 * | 3/2007 | Simonnet | 424/70.31 |

FOREIGN PATENT DOCUMENTS

| | | |
|---|---|---|
| EP | 0 500 437 A1 | 8/1992 |
| EP | 0 647 617 A1 | 4/1995 |
| EP | 0 662 319 A1 | 7/1995 |
| EP | 0 716 849 A1 | 6/1996 |
| EP | 0 847 752 A1 | 6/1998 |
| EP | 0 940 137 A1 | 9/1999 |
| EP | 1 600 152 A1 | 11/2005 |
| EP | 1 272 148 B1 | 6/2006 |
| FR | 2 759 902 A1 | 8/1998 |
| FR | 2 835 430 A1 | 8/2003 |
| FR | 2 855 048 A1 | 11/2004 |
| FR | 2 855 049 A1 | 11/2004 |
| JP | A-4-117317 | 4/1992 |
| JP | A-2008-20755 | 1/2008 |
| WO | WO 99/09936 A1 | 3/1999 |
| WO | WO 99/09937 A1 | 3/1999 |
| WO | WO 01/76538 A1 | 10/2001 |
| WO | WO 01/82861 A2 | 11/2001 |

OTHER PUBLICATIONS

Chun et al (First Asymmetric Synthesis of 6-Hydroxy-4 Sphingenine-Containing Ceramides. Use of Chiral Propargylic Alcohols to Prepare a Lipid Found in Human Skin, J. Org. Chem., 2003, 68 92), pp. 348-354, printed pp. 1-16).*

* cited by examiner

*Primary Examiner* — Sreeni Padmanabhan
*Assistant Examiner* — Timothy E Betton
(74) *Attorney, Agent, or Firm* — Oliff & Berridge, PLC (57) ABSTRACT

The present invention relates to the field of preventive and/or curative protection of delicate lips. More precisely, a subject-matter of the invention is the cosmetic use of active principles which are capable of enhancing the content of ceramides in the lips, such as a ceramide precursor comprising a 6-hydroxy-4-sphingenine base, ascorbic acid or one of its analogues, as protective agent for delicate lips. The invention is additionally targeted at corresponding compositions for labial application.

29 Claims, 1 Drawing Sheet

FIGURE 1

USE OF ACTIVE PRINCIPLES WHICH ARE CAPABLE OF ENHANCING THE CONTENT OF CERAMIDES, AS PROTECTIVE AGENT FOR DELICATE LIPS

This non provisional application claims the benefit of French Applications No. 07 52658 filed on Jan. 12, 2007, French Application No. 07 56522 of Jul. 16, 2007 and U.S. Provisional Application No. 60/902,857 filed on Feb. 23, 2007.

BACKGROUND

The present invention relates to the field of the preventive and/or curative protection of delicate lips.

SUMMARY OF THE INVENTION

The term "delicate lips" is intended to denote, in the context of the present invention, lips capable of being affected by a number of signs or also disorders ranging from feelings of discomfort to cracks, via feelings of smarting and of tightness, the appearance of scales, of dry patches, of chapping or also of bleeding. These signs are more particularly located on the part of the lips referred to as vermilion border or red lips. Epidemiological studies carried out on hundreds of woman in Europe, Asia and North America show that delicate lips are a frequent disorder. Thus, for example, it affects 67% of woman in France and 54% in Japan. This disorder is felt to be severe (very delicate lips) by one woman in 5 in France and one woman in three in Japan.

DETAILED DESCRIPTION

Figure 1:
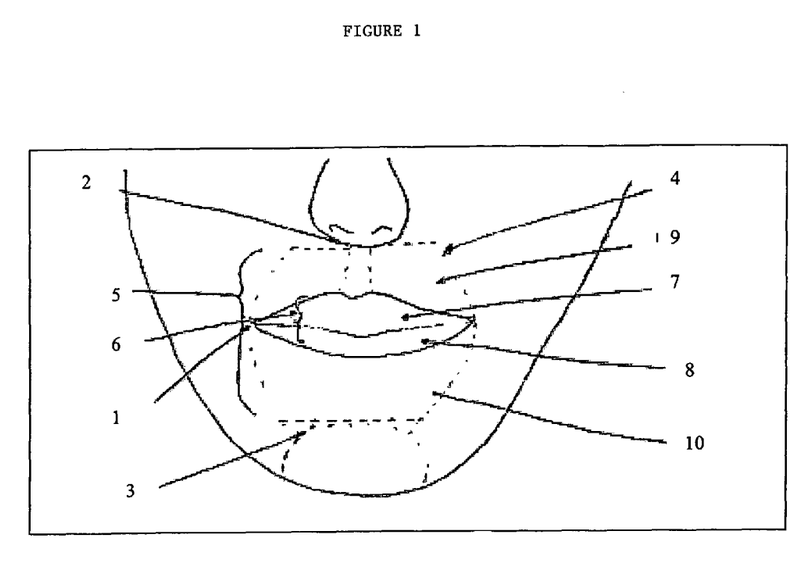
FIG. 1 shows the general anatomy of the perilabial region and the vermilion zone.

The appended FIGURE makes it possible to illustrate this vermilion zone and more generally the anatomy of the perilabial region.

The term "lip" in fact covers an anatomical region of the face referenced 5 in the appended FIGURE, delimited at the top by the nose 2, laterally by the nasogenian grooves 4 and at the bottom by the chin muscle 3. It comprises the upper lip 9 and the lower lip 10. The upper lip and the lower lip come together at their two lateral ends to form the labial commissure 1.

Moreover, three highly differentiated parts are to be distinguished within this anatomical entity:
  a part having a similar appearance to that of the skin of the body. The term used is "white lips",
  a part having an appearance very different from that of the skin of the body.
  The term used is "red lips", also known as vermilion border,
  an endobuccal part of mucus type.

White lips are composed of a conventional cutaneous tissue which is orthokeratinized and covered with an epidermis and with a dermis provided with pilosebaceous follicles and with eccrine sweat glands.

The main role of conventional skin is to establish a protective barrier against attacks from the surroundings while making possible certain exchanges between the internal medium and the external medium. It is composed, from the inside outwards, of the hypodermis, the dermis and the epidermis.

The epidermis is the most superficial layer of the skin, composed predominantly of keratinocytes (90%). The differentiation of the keratinocytes is accompanied by a set of morphological and biochemical conversions which results in the formation of mature cells, the corneocytes. Corneocytes are flattened anucleate cells. They become detached at the surface of the skin according to a desquamation process. This desquamation, where it is physiological, is invisible and does not give rise to the presence of scales visible at the surface of the skin. During their horny maturation, the keratinocytes migrate from the depth towards the surface of the epidermis and form four epidermal layers: the basal layer (stratum basal), the prickle cell layer (stratum spinosum), the granular layer (stratum ganulosum) and the horny layer (stratum corneum), which is the outermost layer, composed of mature corneocytes. This layer builds the first line of defense of the epidermal barrier.

The vermilion border 6 for its part exhibits a very specific structure, in no way comparable to the structure of conventional skin, in several respects.

The vermilion zone or red lips (lower 8 or upper 7) is a structure unique to *Homo sapiens*. It is a zone intermediate between orthokeratinized skin and the mucous membrane. It is composed of a parakeratinized epithelium, that is to say an epithelium exhibiting incomplete keratinization of the corneocytes, some of which still contain nucleate components. The dermis exhibits very numerous and important dermal papillae (forming a physiological hyperpapillomatosis on histological sections).

Moreover, the epithelium of the vermilion border is thicker in comparison with conventional skin and in particular in comparison with the skin of the white lips. In contrast, the stratum corneum (SC) covering the vermilion border is extremely thin. The keratinocytes of the vermilion border have a faster degree of replacement or turnover than in conventional skin. This rapidity results in incomplete differentiation of the corneocytes (incomplete keratinization) and thus in an immature SC comprising nucleate cells (Hikima R. et al., Etude fondamentale des lèvres (II): Relief labial et gercement des levres [Fundamental study of the lips (II): Labial relief and cracking of the lips]. Journal of Japanese Cosmetic Science Society 20[4], 265-69. 1996). The level of these nucleate cells appears positively correlated with the degree of cracking of the lips.

The vermilion border is richly vascularized and rests virtually directly, without a true hypodermal stratum, on the orbicular muscle of the lips, the combination giving this vermilion red colour to this part of the lips. The vermilion borders, unlike the other areas of the cutaneous covering of the body, do not comprise hair follicles, do not comprise sweat glands and comprise few or no sebaceous glands. With regard to the latter, only 50% of individuals have a few sebaceous glands, which appear after adolescence.

Consequently, the physiology of this highly particular area of the skin is very specific and very poorly known. In view of these numerous distinctive features (parakeratosic differentiation, muscular stratum, absence of epidermal adnexa), it is not possible to transpose, to the epidermis of the vermilion border, the knowledge established for the remainder of the cutaneous covering.

Finally, the mucous membrane is an interior area which is covered with a thick nonkeratinized epithelium formed of flattened cells, which is devoid of an SC and which has high permeability. This area is kept continually moist by saliva.

In the continuation of the present description, for reasons of simplicity and although the vermilion zone is the area targeted by the present description, the term "lips" will be used. In other words, in the continuation of the description, unless otherwise indicated, the term "lips" denotes the vermilion borders.

In order to truly apprehend the present invention, the specificity of the vermilion borders, not only in histological terms, as mentioned above, in particular with regard to the skin, but also in terms of ailments or signs of discomfort, and even of pathologies, which may be associated therewith, should thus be noted.

In reality, it could be observed that some women complain of delicate lips throughout the year. They are then regarded as having "very delicate" lips. Others complain of delicate lips only during certain periods of the year, for example the winter. They are then regarded as having "delicate" lips.

Unless otherwise indicated in the description which will follow, the term "delicate lips" employed covers the "delicate" lips and the "very delicate" lips defined above.

In any case, in view of the fact that it is located at the boundary of the digestive and cutaneous sphere, of the numerous contacts with foods and saliva and of its specific structure with a thin and immature stratum corneum, the vermilion border represents, in many people, an area of weakness recognized by the latter.

The signs associated with delicate lips are described in detail below. They can exist separately from one another or be combined.

All these signs may be unpleasant, troublesome and uncomfortable during movements of the lips in the course of speaking or eating. Furthermore, they may prevent lipstick from being used. In the severest cases, where the woman exhibits chapping or bleeding, latter signs may be painful: it is thus worth paying attention thereto with a view to developing appropriate cosmological prevention and/or treatment methods.

Although the combination of these signs is frequently observed, the development of the triggering phenomena is far from being controlled. In particular, the influence of age on the onset of these signs is known (Arais S., et al. Study on lip surface: Characteristics of chapped lip. Journal of Japanese Cosmetic Science Society 13[2], 64-68. 1989).

Furthermore, the lips are continually exposed to the external environment, being subject directly to environmental attacks. For example, the cold and the wind might be desiccating factors for the lips and may contribute to the appearance of delicate lips. The winter season has been shown as being a period more propice to cracking of the lips. UV radiation is also capable of being a cause of delicate lips. In the present world, the widespread use of climate-controlled air might play a role in the onset of delicate lips.

Finally, the lips are directly in contact with various stimulations of a physicochemical nature. For example, eating, lipsticks, addiction to smoking, the tongue, and the like, are among the factors causing delicate lips.

Thus, when it is conventionally a question of protecting the lips, the aim is generally to overcome solely the problem of desiccated lips and the formation of cracks or splits on the lips.

However, as described above, the problem of delicate lips concerns a more complex concept. Thus, delicate lips not only cause mechanical and biochemical damage to the epidermal barrier and anomalies in desquamation but also affect the neurosensory aspect of the lips.

Thus, no person affected by delicate lips within the meaning of the present invention can be satisfied by the products currently employed, namely, in particular, the stick lip balms targeted mainly at moisturizing the lips, which makes it possible to soothe the immediate effects of desiccation or cracking. These lip balms of the prior art can also be criticized for not even demonstrating speed of action, indeed even of not providing a true solution to the problem itself.

Typically, the use is known of lip balms comprising fatty substances, in particular oils or waxes, for example of vegetable origin, petrolatum or also lanolin.

The main aim of these substances is to slow down the loss of water from the lips.

These lip balms can in addition exhibit the disadvantage of conferring a rather unattractive appearance due to mediocre applicational cosmetic properties because of the greasiness and heaviness of the abovementioned moisturizing substances.

Furthermore, the use is known, from the document EP 0 940 137, of acexamic acid as agent which makes it possible to treat and prevent desiccation and formation of cracks and/or splits of the lips.

Ceramides constitute between 47% of the total weight of the lipids of the SC of the skin and are also present in a large amount in the lips.

They are composed of a sphingoid base which can be of four types: sphinganine (also known as dihydrosphingosine), 4-sphingenine (also known as sphingosine), phyotospingosine (also known as 4-hydroxysphinganine) and 6-hydroxy-4-sphingenine (also known as 6-hydroxysphingenine), and of a fatty acid which can be saturated, α-hydroxylated or ω-esterified. The various possible combinations between bases and fatty acids result in approximately ten ceramides listed by Robson, K. J.; Stewart, M. E.; Michelsen, S.; Lazo, N. D.; Downing, D. T., 6-hydroxy-4-sphingenine in human epidermal ceramides, in J. Lipid Res., 1994, 305, 2060-2068, and Chopart M., Castiel-Higounenc I., Arbey E., Guey C., Gaetani Q., Schmidt R., *The normal human stratum corneum: a new ceramide profile, Perspectives in Percutaneous Penetration,* 8th International Conference, Antibes Juan-Les Pins—France, Apr. 2-6, 2002.

A number of natural or synthetic ceramides and their precursors have been proposed as active ingredient in compositions intended to treat cutaneous disorders, such as damage caused by UV radiation or deficiencies in hydration.

The document FR 2 855 049 teaches, the use for reinforcing the barrier function of the skin and in particular for combating cutaneous disorders, such as dry, rough or damaged, indeed even aged, skin, of a composition comprising a substance capable of specifically activating the in vivo synthesis of ceramides comprising a 6-hydroxy-4-sphingenine base, such as, for example, ascorbic acid (vitamin C) and its analogues, associated with a ceramide precursor comprising a sphingenine base, or one of its derivatives.

For its part, the document FR-2 855 048 teaches the use of a combination of at least one ceramide precursor comprising a phytosphingosine base with a substance which activates the 4-hydroxylase pathway in reinforcing the barrier function of the skin as well, and in particular in overcoming cutaneous disorders such as dry, rough, damaged and/or atopic, indeed even aged or sensitive, skin.

Likewise, the document FR-2 835 430 relates to compositions for caring for sensitive skin comprising at least one meth(acrylamide) homopolymer or copolymer and an aqueous suspension of nanocapsules at least partially coated with lecithin.

The documents EP 500 437 and EP 0 647 617 describe synthetic ceramides for the treatment and care of the skin and hair.

With regard to the document EP 0716849, it describes a composition comprising a mixture of ceramides which is intended in particular to moisturize the skin.

The document FR 2 759 902 relates to lipstick sticks comprising, inter alia, ceramides and also having moisturizing properties while behaving well towards makeup.

WO 01/75538 also discloses the use of a composition comprising ceramides for the treatment of lips subjected to xeric stress.

Finally, the document EP 1 272 148 describes the use of a mixture of ceramides, of essential fatty acids and of nonessential fatty acids in defined molar ratios in the manufacture of a medicament for the prevention and the repair of xeric stress of the lips of a human subject by application to the said lips of an amount of the said composition which makes possible maintenance of the barrier function.

The inventors have found, surprisingly, that the appearance of delicate lips within the meaning of the present invention is related to a deficiency of ceramides and in particular of ceramides comprising a 6-hydroxy-4-sphingenine base.

Mention may in particular be made, among ceramides comprising a 6-hydroxy-4-sphingenine base, of ceramide IV, ceramide VII, ceramide 5.5 and ceramide STAR.

The term "ceramide STAR" is intended to denote, within the meaning of the invention, the compounds with the structure:

in which a, b and c are integers varying from 3 to 30, preferably from 8 to 24, and in particular where a varies from 15 to 20, b varies from 7 to 18 and c varies from 10 to 18.

The inventors have thus found that it is possible to make good this deficiency of ceramides in the lips, in particular of ceramides comprising a 6-hydroxy-4-sphingenine base, by using active principles which make it possible to enhance the content of ceramides in the lips, in particular in delicate lips.

They have namely displayed that such active principles may be chosen among a ceramide or ascorbic acid or one of its analogues.

Actually, the inventor have found that a precursor of the ceramides comprising a 6-hydroxy-4-sphingenine base makes it possible to convert in the corresponding ceramide, for example by virtue of hydroxylation reaction in the 6 position by enzymes such as 6-hydroxylase, thus allowing to restore the ceramides content in the lips.

Furthermore, the inventors of the present invention have unexpectedly noted that ascorbic acid and its analogues were efficient in order to prevent and/or treat the clinical signs associated with delicate lips, namely by allowing more rapidly enhancement of the content of ceramides comprising a 6-hydroxy-4-sphingenine base in the lips synthesised from a ceramide precursor comprising a 6-hydroxy-4-sphingenine base naturally present in the lips.

Actually, ascorbic acid and its analogues make it possible to enhance the degree of conversion of target ceramide precursors present naturally in the lips to ceramides comprising a 6-hydroxy-4-sphingenine base.

Thus, according to one of its embodiment, the invention relates to the cosmetic use of active principles which are capable of enhancing the content of ceramides in the lips and in particular of the content of ceramide comprising a 6-hydroxy-4-sphingenine base, as protective agent for delicate lips and in particular in the vermilion zone, it being possible for such an active principle to be chosen from a ceramide precursor comprising a 6-hydroxy-4-sphingenine base or ascorbic acid or at least one of its analogues.

According to a specific embodiment, the invention relates to the cosmetic use of a ceramide precursor comprising a 6-hydroxy-4-sphingenine base, as protective agent for delicate lips and in particular for the vermilion zone.

According to a specific embodiment, the invention relates to the cosmetic use of a ceramide precursor comprising a 6-hydroxy-4-sphingenine base as protective agent for delicate lips and in particular for the vermilion zone.

More particularly, it relates to the cosmetic use of a ceramide precursor compound comprising a 6-hydroxy-4-sphingenine base of the following formula (I):

in which:
  $R_1$ represents a $C_3$ to $C_{30}$, in particular $C_7$ to $C_{25}$ and preferably $C_1$ to $C_2$, alkyl or alkenyl radical, and
  $R_2$ represents a hydrogen atom or a $C_3$ to $C_{30}$, in particular $C_5$ to $C_{25}$ and preferably $C_8$ to $C_{24}$ hydrocarbon radical which is linear and optionally hydroxylated, the hydroxyl group being in the α position with respect to the carbonyl, and which can comprise one or more ethylenic unsaturations, in particular one or two ethylenic unsaturations, or of one of its derivatives, as protective agent for delicate lips, in particular for the vermilion zone.

More specifically, a subject-matter of the invention is the cosmetic use of a ceramide V or of a ceramide V derivative as defined below as protective agent for delicate lips, in particular for the vermilion zone.

According to another embodiment, the invention relates to the cosmetic use of ascorbic acid or of at least one of its analogues as protective agent for delicate lips and in particular of the vermilion zone.

The term ascorbic acid "analogue" is intended to denote, within the meaning of the invention, the salts, the esters, the sugars and the derivatives of ascorbic acid capable of manifesting the same activity as ascorbic acid with regard to protecting delicate lips and in particular with regard to the prevention and/or treatment of the clinical signs associated with delicate lips.

The signs associated with delicate lips and in particular with the delicate vermilion zone are described in detail below. They may exist separately from one another or be combined:
  feeling of discomfort and/or smarting: this is a state with regard to which it is desirable to make a response, of treatment or of care, which makes it possible to better withstand discomfort;
  the feeling of tightness: this is a troublesome feeling of tension on the lips;
  the presence of scales: this concerns small flakes of stratum corneum which become visibly detached from the epidermis;
  dry plaques: they are small areas of the stratum corneum which are thickened and hardened and which become detached as plaques;
  chapping: this concerns small wounds which appear spontaneously in the surface part of the epidermis and which have an appearance of surface cuts perpendicular to the surface of the lips; they do not necessarily result in bleeding; cracks: these concern more significant chapping, the depth of which reaches the deep epidermis and the dermis;

bleeding: this concerns oozing of blood via the chapping or cracks of the lips.

The expression "delicate lips", combines, within the meaning of the invention, the lips, in particular the vermilion zone, affected by at least one of these signs associated with delicate lips, in particular the vermilion zone. Three clinical stages of increasing severity may be schematically described:

stage 1: discomfort and/or smarting and/or tightness;
stage 2: the signs of stage 1 are combined with scales and/or dry plaques;
stage 3: the signs of stage 1 and 2 are combined with chapping and/or cracks and/or bleeding.

The ceramide precursors comprising a 6-hydroxy-4-sphingenine base or else ascorbic acid and its analogues used as protective agent for delicate lips, in particular the vermilion zone, make it possible to specifically prevent the expression, in delicate lips, of the above-mentioned clinical signs and/or to treat lips displaying at least one of these signs and thus to have a repairing effect.

Thus, the ceramide precursor comprising a 6-hydroxy-4-sphingenine base or ascorbic acid or at least one of its analogues makes it possible in particular to prevent and/or to treat the signs associated with delicate lips, in particular the "delicate vermilion zone", of the type consisting of feelings of discomfort and/or smarting and/or tightness.

A ceramide precursor comprising a 6-hydroxy-4-sphingenine base or ascorbic acid or at least one its analogues furthermore make it possible to prevent and/or to treat the signs associated with delicate lips, in particular the vermilion zone, which are expressed by the presence of scales and/or dry plaques.

Finally, a ceramide precursor comprising a 6-hydroxy-4-sphingenine base or ascorbic acid or at least one of its analogues also make it possible to prevent and/or to treat the signs associated with delicate lips, in particular the vermilion zone, of the type consisting of chapping and/or cracks and/or bleeding.

According to one embodiment, the invention thus relates to the cosmetic use of a ceramide precursor compound comprising a 6-hydroxy-4-sphingenine base or of ascorbic acid or at least one of its analogues as agent capable of preventing and/or treating (i) feelings of discomfort and/or smarting and/or tightness, (ii) the presence of scales and/or dry plaques, and/or (iii) chapping and/or cracks and/or bleeding, in particular in subjects having delicate lips.

The invention also relates to a ceramide precursor comprising a 6-hydroxy-4-sphingenine base or else ascorbic acid or at least one of its analogues for their use thereof in the prevention and/or treatment (i) of feelings of discomfort and/or smarting and/or tightness, (ii) of the presence of scales and/or dry plaques, and/or (iii) of chapping and/or cracks and/or bleeding, in particular in subjects having delicate lips.

It preferably relates to the cosmetic use of a ceramide precursor comprising a 6-hydroxy-4-sphingenine base or of ascorbic acid or one of its analogues as agent capable of preventing and/or treating (i) feelings of discomfort and/or smarting and/or tightness and (ii) the presence of scales and/or dry plaques, in particular in subjects having delicate lips.

The invention further relates to a ceramide precursor comprising a 6-hydroxy-4-sphingenine base or ascorbic acid or at least one of its analogues for their use thereof in the prevention and/or treatment (i) of feelings of discomfort and/or smarting and/or tightness and (ii) of the presence of scales and/or dry plaques, in particular in subjects having delicate lips.

A further subject-matter of the present invention is a method for the cosmetic treatment of subjects having delicate lips, in particular the vermilion zone, comprising the application, to the lips of the said subjects, of a composition comprising at least one ceramide precursor comprising a 6-hydroxy-4-sphingenine base or at least ascorbic acid or at least one of its analogues according to the invention.

More specifically, it relates, according to a first embodiment, to a method for the cosmetic treatment of subjects whose lips are affected by feelings of discomfort and/or tightness and/or smarting or are predisposed to exhibit these sensations, comprising the application, to the lips of the said subjects, of a composition comprising at least one ceramide precursor comprising a 6-hydroxy-4-sphingenine base or at least ascorbic acid or at least one of its analogues.

According to a second embodiment, it relates to a method for the cosmetic treatment of subjects whose lips are affected by scales and/or dry plaques associated with or not associated with feeling of discomfort and/or tightness and/or smarting or are predisposed to exhibit these disorders, comprising the application, to the lips of the said subjects, of a composition comprising at least one ceramide precursor comprising a 6-hydroxy-4-sphingenine base or at least ascorbic acid or at least one of its analogues.

According to a third embodiment, it relates to a method for the cosmetic treatment of subjects whose lips are affected by chapping and/or cracks and/or bleeding associated with or not associated with scales and/or dry plaques and/or feeling of discomfort and/or tightness and/or smarting or are predisposed to exhibit these disorders, comprising the application, to the lips of the said subjects, of a composition comprising at least one ceramide precursor comprising a 6-hydroxy-4-sphingenine base or at least ascorbic acid or at least one of its analogues.

An additional subject-matter of the present invention is the use of a ceramide precursor comprising a 6-hydroxy-4-sphingenine base or of ascorbic acid or of at least one of its analogues in the preparation of a composition, namely labial, devoted to the protection of delicate lips and in particular the vermilion zone and intended especially for the treatment and/or prevention of the clinical signs associated with delicate lips, according to the invention.

The instant invention also concerns a cermaide precursor comprising a 6-hydroxy-4-sphingenine base or acid ascorbic or at least one of its analogues for their use as protective agent for delicate lips and in particular the vermilion zone for the treatment and/or prevention of clinical signs associated with delicate lips, according to the invention.

The instant invention further relates to the cosmetic use of a ceramide precursor comprising a 6-hydroxy-4-sphingenine base or ascorbic acid or at least one of its analogues to make good the deficiency of ceramides in the lips, in particular ceramides comprising a 6-hydroxy-4-sphingenine base, in particular in subjects having delicate lips, and more specifically to restore a physiologically acceptable content in ceramides comprising a 6-hydroxy-4-sphingenine base in the lips.

The present invention is also targeted at cosmetic and/or dermatological compositions devoted to a labial application comprising, in a physiologically acceptable medium, a ceramide precursor comprising a 6-hydroxy-4-sphingenine base or ascorbic acid or at least one of its analogues as active principle intended to protect delicate lips and in particular the vermilion zone and in particular to prevent and/or treat the above-mentioned clinical signs.

Within the meaning of the invention, the term "to prevent" means the fact of reducing the risk of onset of a phenomenon.

Generally, ceramide precursors comprising a 6-hydroxy-4-sphingenine base suitable for the instant invention, can namely be ceramides V and their derivatives such as defined hereunder.

Ceramide Precursor Comprising a 6-Hydroxy-4-Sphingenine Base

Within the meaning of the invention:

the term "target ceramides" is intended to denote ceramides or ceramide derivatives comprising a 6-hydroxy-4-sphingenine base, the term "ceramide derivatives" is intended to denote glycosylceramides or cerebrosides (i.e., the combination of a ceramide with a sugar) or sphingomyelins (mainly ceramide phosphorylcholine or ceramide phosphoryl ethanolamine), indeed even the hydrolysed form of ceramide, that is to say the sphingoid base alone or phosphorylated, and the term "ceramide precursors comprising a 6-hydroxy-4-sphingenine base" or also "target ceramide precursors" or also in a more simplified way "ceramide precursors" is understood to mean compounds of ceramide or ceramide derivative type capable of being converted to ceramides or ceramide derivatives comprising a 6-hydroxy-4-sphingenine base, also designated as "target ceramides".

A target ceramide precursor within the meaning of the invention thus denotes a ceramide capable of being converted to a target ceramide, for example by hydroxylation of its 6 position. Such a hydroxylation can, for example, be carried out by 6-hydroxylase, which are enzymes which provide the in vivo synthesis of ceramides or derivatives comprising a 6-hydroxy-4-sphingenine base by hydroxylation in the 6 position of the sphingosine base of target ceramide precursors.

The ceramide precursor or ceramide derivative precursor comprising a 6-hydroxy-4-sphingenine base can be a ceramide or a ceramide derivative comprising a sphingosine base.

The said sphingosine base can then advantageously be of erythro (2S, 3R) conformation.

The ceramide precursor or ceramide derivative precursor comprising a 6-hydroxy-4-sphingenine base can alternatively be a ceramide or a ceramide derivative comprising a sphinganine base.

Generally, it can be a compound of formula (I):

$$R_1\text{—CHOH—CH(NH—COR}_2)(CH_2\text{—OH)} \tag{I}$$

as defined above.

It can in particular be a compound of formula (I) in which $R_1$ represents a $C_{14}$ to $C_{18}$, in particular $C_{15}$, alkyl or alkenyl radical.

It can also be a compound of formula (I) in which $R_2$ represents a $C_{11}$ to $C_{19}$, preferably $C_{15}$ to $C_{19}$, hydrocarbon radical.

Mention may in particular be made, as compound of formula (I) which can be used according to the invention, of N-oleoyldihydrosphingosine (or 2-oleoylamino-1,3-octadecanediol) and ceramides V.

The term "ceramide V" is intended to denote, within the meaning of the invention, any 4-sphingenine or sphinganine acylated by an α-hydroxylated fatty acid having from 4 to 31 carbon atoms, in particular from 6 to 26 carbon atoms, for example from 9 to 25 carbon atoms, preferably from 12 to 20 carbon atoms, and even from 16 to 20 carbon atoms.

The ceramides V can thus be chosen from the compounds of following formulae (IV) and (V):

(IV)

(V)

in which n varies from 1 to 28, in particular from 3 to 23, for example from 6 to 22, preferably from 9 to 17, indeed even from 13 to 17.

Mention may also be made, as ceramide V, of the sphingosine acylated by 2-hydroxystearic acid, also known under the name 2-(2'-hydroxystearoylamino)octadecane-1,3-diol, or also α-hydroxypalmitoyldihydrosphingosine.

According to another embodiment, the present invention concerns a composition for labial application comprising in a physiologically acceptable medium, at least two compounds of formula (I) as defined above.

It can in particular be a composition for labial application comprising, in a physiologically acceptable medium, at least N-oleoyldihydrosphingosine and α-hydroxypalmitoyldihydrosphingosine.

According to another aspect of the present invention, uses and compositions of the invention employ a ceramide precursor such as defined above, as the only cosmetic and/or dermatological active principle or may be combined with one or more other active principles of use or not of use as protective agents for delicate lips, such as defined in the instant invention.

In the context of the present invention, a ceramide precursor comprising a 6-hydroxy-4-sphingenine base, and for example a ceramide V, or one of their derivatives, can be employed in a cosmetic or dermatological composition and in particular in a composition for labial application.

A ceramide precursor comprising a 6-hydroxy-4-sphingenine base, and for example a ceramide V, or one of their derivatives, can be present in a composition for labial application in accordance with the present invention in a content ranging from 0.0001 to 10% by weight, for example from 0.001 to 5% by weight and preferably from 0.05 to 2% by weight, with respect to the total weight of the composition.

As previously mentioned, the ceramide precursor comprising a 6-hydroxy-4-sphingenine base, such as for example cermaide V, may, if appropriate, be the only active principle of use as protective agent for delicate lips.

According to a specific embodiment of the invention, the ceramide precursor comprising a 6-hydroxy-4-sphingenine base may be the only cosmetic and/or dermatological active principle in the composition for labial application. In such a case, such a composition according to the invention may not contain any other additional active principles and in particular may not contain ascorbic acid or one of its analogues.

According to another embodiment of the invention, a ceramide precursor comprising a 6-hydroxy-4-sphingenine base may be associated with further active principles in a composition according to the present invention, said active principles being capable of participating in the exhibition of the desired effect or of providing additional effects, indeed even all other effects, provided that they do not interfere with the exhibition of the desired effect.

The instant invention also relates to a cosmetic method for caring or treating in a non therapeutically manner, lips of human beings, comprising the application to the lips of a composition comprising at least one cermaide precursor comprising a 6-hydroxy4-sphingenine base.

As previously indicated, ascorbic acid (or vitamin C) and its analogues are substances, which activate the 6-hydroxylase pathway, thus capable of enhancing the content of at least one ceramide or derivative of ceramide comprising a 6-hydroxy-4-sphingenine base in the lips in particular delicate lips.

The definition of ascorbic acid and its analogues are more detailed hereunder.

Ascorbic Acid (Vitamin C) and its Analogues

Applied in contact with the lips, a substance which activates the 6-hydroxylase pathway will make it possible to specifically convert the target ceramide precursors present naturally in the lips, and also those contributed by the labial composition, to ceramides or ceramide derivatives comprising a 6-hydroxy-4-sphingenine base.

In order to determine if a substance activates the 6-hydroxylase pathway according to the invention, use may be made of any analytical method which makes it possible to quantify the content in the lips of sphingolipids, advantageously of ceramides or ceramide derivatives, comprising a 6-hydroxy-4-sphingenine base and to measure if this content is enhanced subsequent to the labial application of the said substance.

The ascorbic acid can preferably be in the D or L form, advantageously in the L form, and its analogues be chosen from its salts, preferably sodium ascorbate, magnesium or sodium ascorbyl phosphate, its esters, preferably its acetic, propionic or palmitic esters, or its sugars, preferably glycosylated ascorbic acid, and also the derivatives of formula (II):

(II)

in which:

$R_6$ represents a hydrogen atom, a hydrocarbon chain having from 15 to 20 carbon atoms, a sugar residue, a carbonyl group, an alkyloxycarbonyl group or a carbamoyl group, or else $R_6O$ represents a sulphate functional group or a phosphate functional group, $R_7$ represents a hydrogen atom, a sugar residue or a —$COR_{10}$ group where $R_{10}$ is chosen from:
 (a) a saturated or unsaturated, linear, cyclic or branched, $C_1$-$C_{20}$ hydrocarbon radical which is optionally hydroxylated,
 (b) an optionally hydroxylated aryl radical,
 (c) an aralkyl radical of formula (III):

(III)

where R, R' and R", which are identical or different, represent a hydrogen atom or a hydroxyl, alkoxy, fluoroalkoxy or alkylcarbonyloxy radical, and $R_8$ and $R_9$, which are identical or different, represent a hydrogen atom or a —$COR_{10}$ group as defined above or also, taken together, form an isopropylidene radical, or a salt of this derivative.

The term "sugar residue" is understood to mean, preferably, a glucose, galactose, mannose, fructose or N-acetylglucosamine residue.

The term "saturated, linear or branched, hydrocarbon radical having from 1 to 20 carbon atoms" is understood to mean, for example, a radical chosen from the group consisting of the methyl, ethyl, propyl, isopropyl, butyl, isobutyl, tert-butyl, hexyl, heptyl, 2-ethylhexyl, octyl, nonyl, isononyl, decyl, undecyl, dodecyl, pentadecyl, hexadecyl and octadecyl radicals and preferably the undecyl radical.

In addition, the term "unsaturated, linear or branched, hydrocarbon radical having from 1 to 20 carbon atoms" is understood to mean more particularly a radical chosen from the group consisting of the radicals comprising from 2 to 5 carbon atoms and exhibiting one or more ethylenic unsaturations, in particular the allyl radical.

The preferred substituted or unsubstituted aryl radical is the benzyl radical.

Examples of aralkyl radicals corresponding to the formula (III) above are those in which the aryl group is substituted by: one or more hydroxyl radicals; one or more alkoxy radicals, such as the radical chosen from the group consisting of the methoxy, ethoxy and butoxy radicals, and preferably the methoxy radical; one or more fluoroalkoxy radicals, such as the trifluoromethoxy radical; and one or more alkylcarbonyloxy radicals, such as radicals chosen from the group consisting of the acetoxy, propionyloxy and butyryloxy radicals, and preferably acetoxy.

The ascorbic acid analogues suitable according to the present invention can be chosen from ascorbyl palmitate, magnesium ascorbyl-2-phosphate, glucopyranosyl-L-ascorbic acid, sodium ascorbate, sodium L-ascorbyl-2-phosphate, ascorbyl tetraisopalmitate and the cetyl ether of vitamin C (or vitamin $C_3$-O-hexadecane), and preferably from ascorbyl palmitate and the cetyl ether of vitamin C.

The cetyl ether of vitamin C is in particular available commercially from Nikkol.

According to another embodiment, uses and compositions of the present invention can employ ascorbic acid or at least one of its analogues as the only cosmetic and/or dermatological active principle or may be associated with one or more additional active principles, useful or not as protective agent for delicate lips, as defined in the following text.

As previously indicated, in the context of the present invention, ascorbic acid and/or at least one of its analogues may be employed in a cosmetic or dermatological composition and in particular in a composition for labial application.

Ascorbic acid and/or at least one of its analogues can be present in a composition for labial application in accordance with the present invention in a total content ranging from 0.0001 to 20% by weight, for example from 0.001 to 10% by weight and preferably from 0.01 to 10% by weight, with respect to the total weight of the composition.

As previously indicated, according to another aspect of the invention, ascorbic acid and/or at least one of its analogues may, if appropriate, be the only cosmetic and/or dermatological active principle employed or may be combined with one or more other active principles of use or not of use as protective agent for delicate lips.

According to another embodiment, ascorbic acid and/or at least one of its analogues may be the only active principle(s) of use as protective agent for delicate lips.

According to an embodiment, compositions of the present invention, may comprise ascorbic or one of its analogues, as the only active principle as protective agent for delicate lips. In such a case, compositions of the invention may not comprise any other additional active principle and in particular may not contain for example a ceramide precursor comprising a 6-hydroxy-4-sphingenine base.

According to another aspect of the invention, a composition for labial application of the present invention comprising ascorbic acid and/or at least one of its analogues may further comprise one or more cosmetic and/or dermatological active principles such as defined in the following description.

The present invention also relates to a cosmetic method for caring and treating in a non therapeutically manner the lips of human beings, comprising the application to the lips of a composition such as defined above, comprising at least ascorbic acid or at least one of its analogues.

Moreover, according to another embodiment, the uses and compositions according to the invention can jointly employ ascorbic acid or one of its analogues and at least one ceramide precursor comprising a 6-hydroxy-4-sphingenine base.

Combination of a Ceramide Precursor and Ascorbic Acid Or its Analogues

Applied in contact with the lips, a substance which activates the 6-hydroxylase pathway will make it possible to specifically convert the target ceramide precursors present naturally in the lips, and also those contributed by the labial composition, to ceramides or ceramide derivatives comprising a 6-hydroxy-4-sphingenine base.

By contributing to the lips the substance which activates the 6-hydroxylase pathway and the ceramide precursor, all the components necessary for the production of the target ceramides are thus directly made available to the lips. Thus, the enhancement in the target ceramides will not be made at the expense of the ceramide precursors naturally present in the lips, although it is not ruled out that the latter should also be mobilized by the 6-hydroxylase enzymes. The contribution of ceramide precursors thus makes it possible to access more rapidly and in a larger amount an enhancement in the content of target ceramides in the lips without the natural biosynthesis upstream of the target ceramide precursors being a limiting factor.

Thus, the invention targets the cosmetic use of ascorbic acid or one of its analogues in combination with at least a ceramide precursor comprising a 6-hydroxy-4-sphingenine base, the said combination being of use as protective agent for delicate lips and associated clinical signs as previously defined.

According to another embodiment, the invention relates to a composition for labial application for labial application, comprising in a physiologically acceptable medium, at least one ceramide precursor and in particular a compound of formula (I) as defined above in combination with at least acid ascorbic or at least one of its analogues.

According to the present invention, a labial composition namely comprises in a physiologically acceptable medium, at least acid ascorbic or at least one of its analogues in combination with at least one ceramide precursor according to the present invention, identical or different and preferably different from a ceramide precursor naturally present in the lips.

According to another embodiment, uses and compositions of the present invention can jointly employ ascorbic acid or one of its analogues and at least one ceramide precursor comprising a 6-hydroxy-4-sphingenine base, and/or at least one further additional active principle as hereafter defined, and in particular chosen from at least one natural moisturizing factors deriving from the decomposition of filaggrin.

Cosmetic and/or dermatological active principle comprises a substance acting at the level of the applicational substrate, in this case the lips, which modifies its structure and/or its metabolism by a mechanism of action specific to it. Some of these active principles are in particular described in detail later in the description which follows. Thus, there may also, for example, be involved a protective action on delicate lips but also a healing, soothing, moisturizing or also desquamating action. Typically, the physiologically acceptable medium as defined below or also the structuring agents, film-forming polymers and colouring materials are not active principles. These additional active principles are capable of participating in the exhibition of the desired effect or of providing additional effects, indeed even all other effects, provided that they do not interfere with the exhibition of the desired effect.

As previously indicated, a composition according to the present invention, namely a composition for labial application, may comprise one or more further cosmetic and/or dermatological active principles such as defined hereunder.

Additional Active Principles

According to a specific embodiment, a ceramide precursor comprising a 6-hydroxy-4-sphingenine base or ascorbic acid or at least one of its analogues can be used in combination in the compositions according to the invention with other active principles.

Moisturizing Agents

The term "moisturizing agent" is understood to mean:
- either a compound which has an effect on the barrier function, for the purpose of maintaining the hydration of the stratum corneum, or an occlusive compound. Mention may be made of ceramides other than the ceramide precursors considered above, compounds comprising a sphingoid base, lecithins, glycosphingolipids, phospholipids, cholesterol and its derivatives, phytosterols (stigmasterol, β-sitosterol or campesterol), free fatty acids, essential fatty acids, 1,2 diacylglycerol, petrolatum and lanolin;
- or a compound which directly enhances the water content of the stratum corneum, such as threalose and its derivatives, hyaluronic acid and its derivatives, glycerol, pentanediol, xylitol, glycerol polyacrylate, ectoin and its derivatives, chitosan, oligo- and polysaccharides, such as the products sold under the Pentavitin reference, alginates (in particular the product Sobalg PH 154 sold by Grindsted).

These compounds can represent from 0.001% to 30% and preferably from 0.01 to 20% of the total weight of the composition in accordance with the invention.

In particular, ascorbic acid or one of its analogues can also be used in combination with at least one natural moisturizing factor deriving from the decomposition of filaggrin, itself also of use as active principle as protective agent for delicate lips.

Natural Moisturizing Factors Deriving from the Decomposition of Filaggrin

The term "natural moisturizing factor (or NMF) deriving in particular from the decomposition of filaggrin" is intended to denote, within the meaning of the invention, a compound deriving, that is to say resulting directly or indirectly, from the proteolysis of filaggrin.

Mention may in particular be made, among the NMFs deriving from the decomposition of filaggrin of use according to the invention, of serine, tryptophan, pyrrolidonecarboxylic acid and urocanic acid, and also their salts and their derivatives.

The term "derivatives" is intended to denote the isomers, the esters and the salts of the esters of these compounds, when they exist.

For example, the serine considered according to the invention can be chosen from L-serine, D-serine or (D,L)-serine.

According to one embodiment, the natural moisturizing factor(s) deriving from the decomposition of filaggrin can be chosen from pyrrolidonecarboxylic acid (PCA), its salts, in particular sodium, lysine, arginine, aluminium, magnesium, copper, zinc or magnesium salts, and its derivatives, for example its lipophilic derivatives, in particular menthyl pyrrolidonecarboxylate, its linear or branched $C_2$ to $C_{24}$ and more particularly $C_8$ to $C_{14}$ esters and in particular lauryl, cetyl, octyldodecyl and tetradecyl esters, and the salts of its esters, such as, for example, sodium cocoyl PCA.

Use may in particular be made of the octyldodecyl or of tetradecyl PCA esters sold by Solabia respectively under the references Ceramidone® and Myristidone®, or also the sodium cocoyl PCA sold by Zschimmer and Schwarz under the reference protelan NMA®.

According to one embodiment, the invention thus relates to the cosmetic use of ascorbic acid or of at least one of its analogues as protective agent for delicate lips, in which the latter is used in combination with at least one natural moisturizing factor deriving from the decomposition of filaggrin.

In particular, it relates to the cosmetic use according to the invention in which ascorbic acid or at least one of its analogues is used in combination with serine.

It also relates to the cosmetic use according to the invention in which ascorbic acid or at least one of its analogues is used in combination with tryptophan.

The invention also relates to the cosmetic use according to the invention in which ascorbic acid or at least one of its analogues is used in combination with at least two, in particular at least three, indeed even at least four, natural moisturizing factors deriving from the decomposition of filaggrin.

Thus, it relates in particular to the cosmetic use according to the invention in which ascorbic acid or at least one of its analogues is used in combination with serine and with tryptophan.

The invention also relates to the cosmetic use according to the invention in which ascorbic acid or at least one of its analogues is used in combination with serine, with tryptophan and with pyrrolidonecarboxylic acid, and also with serine, with tryptophan and with urocanic acid, or also with serine, with pyrrolidonecarboxylic acid and with urocanic acid, or also with tryptophan, with pyrrolidonecarboxylic acid with urocanic acid.

The invention also relates to the compositions comprising the combinations described above.

In particular, the invention relates, according to one of its aspects, to the cosmetic use of ascorbic acid or at least one of its analogues in combination at least with a natural moisturizing factor deriving from the decomposition of filaggrin and/or with a ceramide precursor comprising a 6-hydroxy-4-sphingenine base as protective agent for delicate lips, in particular the vermilion zone.

The additional active principles capable of providing additional effects can also belong to the family of the moisturizing agents, desquamating agents, agents for combating pollution or free radicals, soothing agents and healing agents.

Desquamating Agents

The term "desquamating agent" is understood to mean any compound capable of having an effect:

either directly on desquamation by promoting exfoliation, such as β-hydroxy acids, in particular salicylic acid and its derivatives (including 5-(n-octanoyl)salicylic acid); α-hydroxy acids, such as glycolic acid, tartaric acid, malic acid or mandelic acid; gentisic acid; oligofucoses; cinnamic acid; Saphorajaponica extract; resveratrol and certain jasmonic acid derivatives;

or on the enzymes involved in desquamation or decomposition of the comeodesmosomes, such as glycosidases, stratum corneum chymotryptic enzyme (SCCE) or indeed even other proteases (trypsin, chymotrypsin-like). Mention may be made of agents which chelate inorganic salts: EDTA; N-acyl-N,N',N'-ethylenediaminetriacetic acid; aminosulphonic compounds and in particular 4-(2-hydroxyethyl)piperazine-1-propanesulphonic acid (HEPES); 2-oxothiazolidine-4-carboxylic acid (procysteine) derivatives; or sugar derivatives, such as O-octanoyl-6-D-maltose and N-acetylglucosamine.

Agent for Combating Pollution or Free Radicals

The expression "agent for combating pollution" is understood to mean any compound capable of scavenging ozone, mono- or polycyclic aromatic compounds, such as benzopyrene and/or heavy metals, such as cobalt, mercury, cadmium and/or nickel. The term "agent for combating free radicals" is understood to mean any compound capable of scavenging free radicals.

Mention may in particular be made, as scavengers for ozone which can be used in the composition according to the invention, of: phenols and polyphenols, in particular tannins, ellagic acid and tannic acid; epigallocatechin and the natural extracts comprising it; olive tree leaf extracts; tea extracts, in particular green tea extracts; anthocyanins; rosemary extracts; phenolic acids, in particular chorogenic acid; stilbenes, in particular resveratrol; chelating agents, such as N,N'-bis(3,4,5-trimethoxybenzyl)ethylenediamine or one of its salts, metal complexes or esters; or carotenoids, such as crocetin.

Mention may in particular be made, as scavengers for mono- or polycyclic aromatic compounds which can be used in the composition according to the invention, of tannins, such as ellagic acid; indole derivatives, in particular indole-3-carbinol; tea extracts, in particular green tea extracts, water hyacinth or Eichornia crassipes extracts.

Finally, mention may in particular be made, as scavengers for heavy metals which can be used in the composition according to the invention, of chelating agents, such as EDTA, the pentasodium salt of ethylenediamine tetramethylenephosphonic acid, and N,N'-bis(3,4,5-trimethoxybenzyl) ethylenediamine or one of its salts, metal complexes or esters; phytic acid; chitosan derivatives; tea extracts, in particular green tea extracts; or tannins, such as ellagic acid.

The agents for combating free radicals which can be used in the composition according to the invention comprise, in addition to some agents for combating pollution mentioned above, vitamin E and its derivatives, such as tocopheryl acetate; bioflavonoids; coenzyme Q10 or ubiquinone; certain enzymes, such as catalase, superoxide dismutase and the wheat germ extracts comprising it, lactoperoxidase, glutathione peroxidase and quinone reductases; glutathione; benzylidenecamphor; benzylcyclanones; substituted naphthalenones; phytantriol; gamma-oryzanol; guanosine; lignans; and melatonin.

Soothing Agents

Mention may be made, as soothing agents which can be used in the composition in accordance with the invention, of: pentacyclic triterpenes and the plant extracts (e.g. Glycyrrhiza glabra) comprising them, such as β-glycyrrhetinic acid and its salts and/or its derivatives (glycyrrhetinic acid monoglucuronide, stearyl glycyrrhetinate, 3-stearoyloxyglycyrrhetic acid), ursolic acid and its salts; oleanolic acid and its salts, betulinic acid and its salts, plant extracts, such as of *Paeonia suffruticosa* and/or *lactiflora, Laminaria saccharina, Boswellia serrata, Centipeda cunnighami, Helianthus annuus, Linum usitatissimum, Cola nitida, Epilobium angustifolium, Aloe vera* or *Bacopa monieri*, salicylic acid salts and in particular zinc salicylate, canola oil, bisabolol and camomile extracts, allantoin, Sepivital EPC (phosphoric diester of vitamin A) from Seppic, omega-3 unsaturated oils, such as musk rose oil, blackcurrant oil, Echium oil or fish oil, plankton extracts, tocotrienols, piperonal, a clove extract, phytosterols, cortisone, hydrocortisone, indomethacin and betamethasone.

Healing Agents

Examples of healing agents are in particular the fern leaf extracts sold under the reference Mamaku Vital Essence® by Lucas Meyer, the rice peptides obtained by hydrolysis of rice proteins sold under the name Nutripeptide® by Silab, zinc oxide or vitamin B5.

Mention may in particular be made, among the active principles which do not provide an additional effect but which provide effects other than the protective effects for delicate lips, provided that they do not interfere with the exhibition of the desired effect, of:

compounds promoting blood microcirculation, such as agents promoting the production of nitrogen monoxide; antihypertensive agents, in particular potassium channel openers; agents which exhibit phosphodiesterases; flavonoids or flavoglycosides; glucosides, such as C-β-D-xylopyranoside-2-hydroxypropane; plant extracts with vasodilating properties; other vasodilating agents and temperature-modulating agents, muscle-relaxing compounds, such as magnesium gluconate, manganese gluconate and rose extract.

Mention may also be made, as other specific combinations which can be employed in the context of the present invention, of the combinations of an active principle capable of enhancing the ceramide content such as defined in the present invention and in particular chosen among ascorbic acid or at least one of its analogues or a ceramide precursor, such as for example, a ceramide V or a ceramide V derivative, with at least one additional active principle chosen from Centella asiatica extracts, madecassoside, vitamin B5, hydroxyethylurea, zinc oxide and C-β-D-xylopyranoside-2-hydroxypropane.

The additional active principle or principles which may be used in combination with the ceramide precursor can be present in a total content ranging from 0.001 to 30% by weight, in particular from 0.01 to 20% by weight, with respect to the total weight of the composition.

The additional active principle or principles which can be used in combination with ascorbic acid or with one of its analogues can be present in a total content ranging from 0.001 to 30% by weight, in particular from 0.01 to 20% by weight, with respect to the total weight of the composition.

Generally, a ceramide precursor of the invention, ascorbic acid and/or one of its analogues, in combination or not in combination with another active principle, in particular as defined above, are employed in a physiologically acceptable medium in the form of a composition.

Physiologically Acceptable Medium

The term "physiologically acceptable medium" is understood to mean a medium compatible with the lips, such as the oils or the organic solvents commonly employed in cosmetic compositions.

These oils can be present in a content ranging from 0.01 to 90% by weight and better still from 0.1 to 85% by weight, with respect to the total weight of the composition.

The physiologically acceptable medium of the composition according to the invention can also comprise one or more physiological acceptable organic solvents (acceptable tolerance, acceptable toxicology and acceptable feel).

The nonaqueous organic solvent is preferably a compound which is insoluble in water and which is liquid at ambient temperature and atmospheric pressure.

The physiologically acceptable medium can comprise a hydrophilic medium comprising water or a mixture of water and of hydrophilic organic solvent(s), such as alcohols and in particular linear or branched lower monoalcohols having from 2 to 5 carbon atoms, such as ethanol, isopropanol or n-propanol, diglycerol, propylene glycol, sorbitol, pentylene glycol and polyethylene glycols, or alternatively hydrophilic $C_2$ ethers and $C_2$-$C_4$ aldehydes.

The composition according to the invention can also be substantially devoid of such a hydrophilic medium. The composition according to the invention can comprise less than 5% by weight, and even less than 2% by weight, of water, with respect to the total weight of the composition and can in particular be anhydrous.

Solvent Phase

The nonaqueous solvent phase formed by the oils and solvents is capable of forming a continuous phase.

The term "volatile compound" is understood to mean, within the meaning of the invention, any compound (or nonaqueous medium) capable of evaporating on contact with the lips in less than one hour, at ambient temperature and atmospheric pressure. The volatile compound is a volatile cosmetic compound which is liquid at ambient temperature and which has in particular a nonzero vapour pressure at ambient temperature and atmospheric pressure, in particular which has a vapour pressure ranging from 0.13 Pa to 40 000 Pa ($10^{-3}$ to 300 mmHg), especially ranging from 1.3 Pa to 13 000 Pa (0.01 to 100 mmHg), and more particularly ranging from 1.3 Pa to 1300 Pa (0.01 to 10 mmHg).

In contrast, the term "nonvolatile compound" is understood to mean a compound which remains on the lips at ambient temperature and atmospheric pressure for at least several hours and which has in particular a vapour pressure of less than $10^{-3}$ mmHg (0.13 Pa).

The volatile compound which is insoluble in water and which is liquid at ambient temperature is in particular a physiologically acceptable oil (fatty substance which is liquid at 25° C. at atmospheric pressure) or organic solvent.

The volatile oils can be hydrocarbon oils, silicone oils, fluorinated oils or their mixtures.

The term "hydrocarbon oil" is understood to mean an oil mainly comprising hydrogen and carbon atoms and optionally oxygen, nitrogen, sulphur or phosphorus atoms. Volatile hydrocarbon oils can be chosen from hydrocarbon oils having from 8 to 16 carbon atoms and in particular branched $C_8$-$C_{16}$ alkanes, such as $C_8$-$C_{16}$ isoalkanes of petroleum origin (also known as isoparaffins), such as isododecane (also known as 2,2,4,4,6-pentamethylheptane), isodecane, isohexadecane and, for example, the oils sold under the "Isopar®" or "Permethyl®" trade names, branched $C_8$-$C_{16}$ esters, isohexyl neopentanoate, and their mixtures. Other volatile hydrocarbon oils, such as petroleum distillates, in particular those sold under the name "Shell Solt®" by Shell, can also be used.

Use may also be made, as volatile oils, of volatile silicones, such as, for example, volatile linear or cyclic silicone oils, in particular those having a viscosity of less than 8 centistokes and having in particular from 2 to 10 silicon atoms, these silicones optionally comprising alkyl or alkoxy groups having from 1 to 22 carbon atoms. Mention may in particular be made, as volatile silicone oils which can be used in the invention, of octamethylcyclotetrasiloxane, decamethylcyclopentasiloxane, dodecamethylcyclohexasiloxane, heptamethylhexyltrisiloxane, heptamethyloctyltrisiloxane, hexamethyldisiloxane, octamethyltrisiloxane, decamethyltetrasiloxane, dodecamethylpentasiloxane and their mixtures.

The nonaqueous solvent phase can also comprise at least one non-volatile compound which is insoluble in water and which is liquid at ambient temperature, in particular at least one non-volatile oil which can in particular be chosen from non-volatile and preferably glossy hydrocarbon and/or silicone and/or fluorinated oils.

Mention may in particular be made, as non-volatile hydrocarbon oil, of:

- hydrocarbon oils of vegetable origin, such as triglycerides composed of esters of fatty acids and of glycerol, the fatty acids of which can have varied chain lengths from $C_4$ to $C_{24}$, it being possible for these chains to be linear or branched and saturated or unsaturated; these oils are in particular wheat germ, sunflower, grape seed, sesame, maize, apricot, castor, shea, avocado, olive, soybean, sweet almond, palm, rapeseed, cottonseed, hazelnut, macadamia, jojoba, alfalfa, poppy, pumpkinseed, cucumber, blackcurrant, evening primrose, millet, barley, quinoa, rye, safflower, candlenut, passion flower or musk rose oils; or triglycerides of caprylic/capric acids, such as those sold by Stearineries Dubois or those sold under the names "Miglyol 810®", "812®" and "818®" by Dynamit Nobel;
- synthetic ethers having from 10 to 40 carbon atoms;
- linear or branched hydrocarbons of mineral or synthetic origin, such as petrolatum, polydecenes, hydrogenated polyisobutene, such as parleam, squalane and their mixtures;
- synthetic esters, such as oils of formula $R_1COOR_2$ in which $R_1$ represents the residue of a linear or branched fatty acid comprising from 1 to 40 carbon atoms and $R_2$ represents the hydrocarbon chain, in particular a branched hydrocarbon chain, comprising from 1 to 40 carbon atoms, provided the $R_1+R_2$ is $\geq 10$, such as, for example, purcellin oil (cetearyl octanoate), isopropyl myristate, isopropyl palmitate, $C_{12}$ to $C_{15}$ alkyl benzoate, hexyl laurate, diisopropyl adipate, isononyl isononanoate, 2-ethylhexyl palmitate, isostearyl isostearate, or octanoates, decanoates or ricinoleates of alcohols or of polyalcohols, such as propylene glycol dioctanoate; hydroxylated esters, such as isostearyl lactate or diisostearyl malate; and pentaerythritol esters;
- fatty alcohols which are liquid at ambient temperature and which have a branched and/or unsaturated carbon chain having from 12 to 26 carbon atoms, such as octyldodecanol, isostearyl alcohol, oleyl alcohol, 2-hexyldecanol, 2-butyloctanol or 2-undecylpentadecanol;
- higher fatty acids, such as oleic acid, linoleic acid, linolenic acid and their mixtures.

The non-volatile silicone oils which can be used according to the invention can be polydimethylsiloxanes (PDMSs) which are non-volatile, polydimethylsiloxanes comprising pendant alkyl or alkoxy groups and/or alkyl or alkoxy groups at the silicone chain end, which groups each have from 2 to 24 carbon atoms, phenylated silicones, such as phenyl trimethicones, phenyl dimethicones, phenyl trimethylsiloxy diphenylsiloxanes, diphenyl dimethicones, diphenyl methyldiphenyl trisiloxanes or 2-phenylethyl trimethylsiloxysilicates.

The fluorinated oils which can be used in the composition in accordance with the invention are in particular fluorosilicone oils, fluorinated polyethers or fluorinated silicones, such as described in the document EP-A-847752.

Thickening/Structuring Agents

The compositions in accordance with the invention can be provided in the thickened form, in particular anhydrous thickened form, for example in the form of a stick. They can thickened with at least one thickening agent chosen from fatty-phase gelling agents, waxes, pasty fatty substances, fillers and their mixtures.

Mention may be made, as fat-phase gelling agent, of optionally modified clays, such as hectorites modified by a $C_{10}$ to $C_{22}$ fatty acid ammonium chloride, such as hectorite modified by distearyldimethylammonium chloride; silica; partially or completely crosslinked organopolysiloxane elastomers with a three-dimensional structure, such as those sold under the names KSG6, KSG16 or KSG18 by Shin-Etsu, Trefil E-505C or Trefil E-506C by Dow Corning, Gransil SR-CYC, SR DMF10, SR-DC556, SR 5CYC gel, SR DMF 10 gel, SR DC 556 gel by Grant Industries, or SF 1204 and JK 113 by General Electric; galactomannans comprising one to six and better still from two to four hydroxyl groups per monosaccharide, which are substituted by a saturated or unsaturated alkyl chain, such as guar gum alkylated by $C_1$ to $C_6$ and better still $C_1$ to $C_3$ alkyl chains and more particularly ethylenated guar having a degree of substitution of 2 to 3, such as that sold by Aqualon under the name N-Hance AG; gums, in particular silicone gums, such as polydimethylsiloxane PDMSs having a viscosity >500 000 centistokes and/or a molecular weight of greater than or equal to 200 000 g/mol; or silicone polyamides.

Use may also be made of silicone polyamides of the polyorganosiloxane type, such as those described in the documents U.S. Pat. Nos. 5,874,069, 5,919,441, 6,051,216 and U.S. Pat. No. 5,981,680.

These silicone polymers can belong to the following two families:
- polyorganosiloxanes comprising at least two groups capable of establishing hydrogen interactions, these two groups being situated in the chain of the polymer, and/or
- polyorganosiloxanes comprising at least two groups capable of establishing hydrogen interactions, these two groups being situated on grafts or branchings.

These gelling agents are used, for example, at concentrations of 0.05 to 15% of the total weight of the composition.

The compositions in accordance with the invention can comprise at least one wax.

The term "wax" is understood to mean, within the meaning of the present invention, a lipophilic fatty compound which is solid at ambient temperature (25° C.), with a reversible solid/liquid changing state, which has a melting point of greater than 30° C. which can range up to 200° C., which has a hardness of greater than 0.5 MPa and which exhibits, in the solid state, an anisotropic crystalline arrangement. On bringing the wax to its melting point, it is possible to render it miscible with the oils and to form a microscopically homogeneous mixture but, on returning the temperature of the mixture to ambient temperature, recrystallization of the wax in the oils of the mixture is obtained.

The waxes which can be used in the invention are compounds which are solid at ambient temperature and which are intended to structure the composition, in particular in the stick form; they can be hydrocarbon, fluorinated and/or silicone waxes and can be of vegetable, mineral, animal and/or synthetic origin. In particular, they exhibit a melting point of greater than 40° C. and better still of greater than 45° C.

Mention may be made, as wax which can be used in the invention, of those generally used in the cosmetics field: they are in particular of natural origin, such as beeswax, carnauba, candelilla, ouricury, japan, cork fibre or sugarcane, rice or montan wax, paraffin wax, lignite or microcrystalline waxes, ceresin or ozokerite, hydrogenated oils, such as jojoba oil; synthetic waxes, such as the polyethylene waxes resulting from the polymerization or copolymerization of ethylene and Fischer-Tropsch waxes or also fatty acid esters, such as octacosanyl stearate, glycerides which are solid at 40° C. and better still at 45° C., silicone waxes, such as alkyl or alkoxy dimethicones having an alkyl or alkoxy chain of 10 to 45 carbon atoms, poly(di)methylsiloxane esters which are solid at 40° C., the ester chain of which comprises at least 10 carbon atoms; and their mixtures.

The compositions in accordance with the invention advantageously comprise polyethylene wax with a weight-average molecular weight of between 300 and 700 g/mol, in particular equal to 500 g/mol.

By way of indication, the wax can represent from 0.01 to 50%, preferably from 2 to 40% and better still from 5 to 30% of the total weight of the composition.

The compositions in accordance with the invention can also comprise at least one pasty compound.

The term "pasty" is understood to denote, within the meaning of the present invention, a lipophilic fatty compound exhibiting a reversible solid/liquid changing state and comprising, at a temperature of 23° C., a liquid fraction and a solid fraction. The term "pasty" is also understood to mean polyvinyl laurate.

The pasty compound is advantageously chosen from:
polymeric or nonpolymeric fluorinated compounds,
polymeric or nonpolymeric silicone compounds,
vinyl polymers,
olefin homopolymers,
olefin copolymers,
hydrogenated diene homopolymers and copolymers,
linear or branched and homo- or copolymeric oligomers of alkyl (meth)acrylates preferably having a $C_8$-$C_{30}$ alkyl group,
homo- and copolymeric oligomers of vinyl esters having $C_8$-$C_{30}$ alkyl groups,
homo- and copolymeric oligomers of vinyl ethers having $C_8$-$C_{30}$ alkyl groups,
fat-soluble polyethers resulting from polyetherification between one or more $C_2$-$C_{100}$, preferably $C_2$-$C_{50}$, diols,
esters,
their mixtures.

Among fat-soluble polyethers, preference is given in particular to copolymers of ethylene oxide and/or of propylene oxide with long-chain $C_6$-$C_{30}$ alkylene oxides, more preferably such that the ratio by weight of the ethylene oxide and/or propylene oxide with alkylene oxides in the copolymer is from 5:95 to 70:30. In this family, mention will in particular be made of the copolymers such that the long-chain alkylene oxides are arranged in blocks having an average molecular weight from 1000 to 10 000, for example a polyoxyethylene/polydodecyl glycol block copolymer, such as the ethers of dodecanediol (22 mol) and of polyethylene glycol (45 EO) sold under the Elfacos ST9 brand by Akzo Nobel.

Preference is in particular given, among pasty esters, to:
the esters of an oligomeric glycerol, in particular the esters of diglycerol, in particular the condensates of adipic acid and of glycerol, for which a portion of the hydroxyl groups of the glycerols have reacted with a mixture of fatty acids, such as stearic acid, capric acid, stearic acid and isostearic acid and 12-hydroxystearic acid, such as in particular those sold under the Softisan 649 brand by Sasol,
the arachidyl propionate sold under the Waxenol 801 brand by Alzo,
phytosterol esters,
noncrossed linked polyesters resulting from the polycondensation between a linear or branched $C_4$-$C_{50}$ di- or polycarboxylic acid and a $C_2$-$C_{50}$ diol or polyol, other than the polyester described above,
aliphatic esters of an ester resulting from the esterification of an aliphatic hydroxycarboxylic acid ester by an aliphatic monocarboxylic acid, and their mixtures, such as
the ester resulting from the esterification reaction of hydrogenated castor oil with isostearic acid in their proportions of 1 to 1 (1/1) or hydrogenated castor oil monostearate,
the ester resulting from the esterification reaction of hydrogenated castor oil with isostearic acid in their proportions of 1 to 2 (1/2) or hydrogenated castor oil diisostearate,
the ester resulting from the esterification reaction of hydrogenated castor oil with isostearic acid in their proportion of 1 to 3 (1/3) or hydrogenated castor oil triisostearate,
and their mixtures.

The choice will preferably be made, among pasty compounds of vegetable origin, of a mixture of soya sterols and of oxyethylated (5 EO) oxypropylated (5 PO) pentaerythritol, sold under the reference Lanolide by Vevy.

The pasty compound preferably represents 1 to 99% by weight, better still 1 to 60% by weight, better still 2 to 30% by weight and even better still 5 to 20% by weight of the composition.

As specified above, the compositions according to the invention can also comprise one or more fillers, in particular in a content ranging from 0.01% to 50% by weight, with respect to the total weight of the composition, preferably ranging from 0.01% to 30% by weight.

The term "fillers" should be understood as meaning colourless or white and inorganic or synthetic particles in any shape which are insoluble in the medium of the composition, whatever the temperature in which the composition is manufactured. These fillers are used in particular to modify the rheology or the texture of the composition.

The fillers can be inorganic or organic and of any shape, platelet, spherical or oblong. Mention may be made of talc, mica, silica, kaolin, polyamide (Nylon®) powders (Orgasol® from Atochem), poly-β-alanine powders, polyethylene powders, powders formed of tetrafluoroethylene polymers (Teflon®), lauroyllysine, starch, boron nitride, polymeric hollow microspheres, such as those of polyvinylidene chloride/acrylonitrile, such as Expancel® (Nobel Industrie), or of acrylic acid copolymers (Polytrap® 603 from Dow Corning), silicone resin microbeads (Tospearls® from Toshiba, for example), polyorganosiloxane elastomer particles, precipitated calcium carbonate, magnesium carbonate, basic magnesium carbonate, hydroxyapatite, hollow silica microspheres (Silica Beads® from Maprecos), glass or ceramic microcapsules, metal soaps derived from organic carboxylic acids having from 8 to 22 carbon atoms, preferably from 12 to 18 carbon atoms, for example zinc stearate, magnesium stearate, lithium stearate, zinc laurate or magnesium myristate, or Polypore® L 200 (Chemdal Corporation). Mention may also be made of silica-based fillers, such as Aerosil 200, or Aerosil 300; Sunsphare L-31, or Sunphare H-31, sold by Asahi Glass; Chemicelen, sold by Asahi Chemical; or composites of silica and of titanium dioxide, such as the TSG series sold by Nippon Sheet Glass. Finally, mention may be made of polyurethane powders, in particular powders formed of crosslinked polyurethane comprising a copolymer, the said copolymer comprising trimethylol hexyllactone. In particular, a hexamethylene diisocyanate/trimethylol hexyllactone polymer may be involved. Such particles are in particular available commercially, for example under the name of Plastic Powder D-400® or Plastic Powder D-800® from Toshiki.

Colouring Material

According to a specific embodiment, the compositions in accordance with the invention comprise at least one colouring material which can be chosen from dyes, pigments, pearlescent agents and their mixtures. This colouring material can represent from 0.001 to 98%, preferably from 0.1 to 85% and in particular from 0.5 to 60% of the total weight of the composition.

For obvious reasons, these colouring materials are employed in the compositions in accordance with the invention so as not to prejudice the effect more particularly desired according to the invention and which is targeted in particular at providing protection for delicate lips.

For a composition in the paste or cast form, such as lipsticks, use is generally made of 0.5 to 50% of colouring material, preferably of 2 to 40% and in particular 5 to 30%, with respect to the total weight of the composition.

The dyes are preferably fat-soluble dyes, although water-soluble dyes can be used. The fat-soluble dyes are, for example, Sudan Red, D & C Red 17, D & C Green 6, β-carotene, soybean oil, Sudan brown, D & C Yellow 11, D & C Violet 2, D & C Orange 5, quinoline Yellow or annatto. They can represent from 0 to 20% of the weight of the composition and better still from 0.1 to 6%. The water-soluble dyes are in particular beetroot juice or methylene blue and can represent from 0.01 to 6% by weight of the composition (if present).

The term "pigments" should be understood as meaning white or coloured and inorganic or organic particles which are insoluble in the liquid fatty phase and which are intended to colour and/or to opacify the composition. The term "pearlescent agents" should be understood as meaning iridescent particles, in particular produced by certain shellfish in their shells or else synthesized.

The pigments can be present in the composition in a proportion of 0.05 to 30% of the weight of the final composition and preferably in a proportion of 0.1 to 20%. Mention may be made, as inorganic pigments which can be used in the invention, of titanium, zirconium or cerium oxides and also zinc, iron or chromium oxides and ferrite blue. Mention may be made, among the organic pigments which can be used in the invention, of carbon black and baryum, strontium, calcium (D & C Red No. 7) and aluminium lakes.

The pearlescent agents can be present in the composition in a proportion of 0.001 to 20% of the total weight of the composition, preferably at a level of the order of 1 to 15%. Mention may be made, among the pearlescent agents which can be used in the invention, of mica covered with titanium oxide, with iron oxide, with natural pigment or with bismuth oxychloride, such as coloured titanium oxide-coated mica.

The compositions can also advantageously comprise goniochromatic pigments, for example interferential multilayer pigments, and/or reflecting pigments. These two types of pigments are described in the document FR0209 246, the content of which is incorporated by reference in the present patent application.

Film-Forming Polymer

The composition can additionally comprise a film-forming polymer.

According to the present invention, the term "film-forming polymer" is understood to mean a polymer capable of forming, by itself alone or in the presence of an additional agent which is able to form a film, a continuous film which adheres to the lips.

Mention may be made, among the film-forming polymers which can be used in the composition in accordance with the present invention, of synthetic polymers of radical type or of polycondensate type, polymers of natural origin and their mixtures. Mention may in particular be made, as film-forming polymer, of acrylic polymers, polyurethanes, polyesters, polyamides, polyureas or cellulose polymers, such as nitrocellulose.

The polymer can be used in combination with one or more additional agents which are able to form a film. Such an agent which is able to form a film can be chosen from all the compounds known to a person skilled in the art as being capable of fulfilling the desired role and in particular can be chosen from plasticizing agents and coalescence agents.

The composition in accordance with the invention can additionally comprise any ingredient normally used in the field of the care of the lips, such as essential oils, preservatives, fragrances, neutralizing agents, fat-soluble polymers, in particular hydrocarbon polymers, such as polyalkylenes or polyvinyl laurate, aqueous-phase gelling agents, surfactants, emollients, tightening agents, vitamins, essential fatty acids, lipophilic or hydrophilic sunscreens, and their mixtures.

Of course, a person skilled in the art will take care to choose the optional additional ingredients and/or their amounts in such a way that the advantageous properties of the composition in accordance with the invention are not, or not substantially, detrimentally affected by the addition.

A composition of the invention can be provided in the form of a paste, in particular of a soft paste, of a solid, of a cream, of a foam, of a spray, of a powder or even of a liquid. It can be an oil-in-water (O/W), oil-in-polyol, water-in-oil (W/O) or water-in-polyol emulsion, a multiple (W/O/W or polyol/O/W or O/W/O) emulsion, an anhydrous gel, a soft paste or solid, a liquid oily phase, a suspension, a dispersion or a solution. Preferably, it is provided in the form of an anhydrous solid composition and more especially in the form of a stick.

A person skilled in the art can choose the appropriate formulation form and also its method of preparation on the basis of his or her general knowledge, taking into account, on the one hand, the nature of the constituents used, in particular their solubility in the substrate, and, on the other hand, the application envisaged for the composition.

According to a specific embodiment, a composition in accordance with the invention can be provided in the anhydrous thick form. Consequently, the invention more especially relates to a thickened anhydrous composition for making up or caring for delicate lips comprising at least one thickening agent chosen from fatty-phase gelling agents, waxes, fillers and their mixtures as described in detail below.

A composition in accordance with the invention can be provided in the form of a dermatological composition or of a care composition for the lips, or in the form of a composition for the antisun protection of the lips. It is then provided in the colourless form, optionally comprising cosmetic or dermatological active principles, other than the ceramide precursor, as described in detail below. It can then be used in the form of a care base for delicate lips. It can in particular take the form of a lip balm, in particular protecting the lips from the intrinsic and external factors capable of promoting the onset of delicate lips. Mention may in particular be made, among these external factors, of cold, UV radiation, wind and physicochemical stimulations, such as the eating of meals, lipsticks, addiction to smoking and the tongue.

The composition in accordance with the invention can also be provided in the form of a coloured product for making up the lips, such as a lipstick or a lip gloss, exhibiting care and/or treatment properties.

Of course, the composition in accordance with the invention must be cosmetically or dermatologically acceptable, namely non-toxic and capable of being applied to lips of human beings.

According to another embodiment, a composition in accordance with the invention can be provided in a form compatible with buccal administration. According to this alternative, it is applied to the lips by bringing the latter into contact with a saliva comprising it.

A further subject-matter of the present invention is a cosmetic method for the care or nontherapeutic treatment of the lips of human beings comprising the application, to the lips, of the composition as defined above.

The invention is illustrated in more detail by the following examples, without being limited to them. The percentages are given by weight.

EXAMPLE 1

Coloured Lipstick Stick for Delicate Lips

| | |
|---|---|
| Castor oil | 3% |
| Liquid petrolatum | 9% |
| Lanoline | 15% |
| Beeswax | 9% |
| Ozokerite | 10% |
| α-Hydroxypalmitoyldihydrosphingosine | 0.24% |
| Ascorbyl palmitate | 0.2% |
| Soybean lecithin | 7% |
| Glycerol | 8% |
| Talc | 3% |
| D&C Red 27 | 5% |
| D&C Red 7 | 6% |
| Black iron oxide | 2% |
| Polybutene | q.s. for 100% |
| Fragrance | q.s |

EXAMPLE 2

Colourless Lipstick for Delicate Lips

| | |
|---|---|
| Castor oil | 20% |
| Jojoba oil | q.s. for 100% |
| Isopropyl lanolate | 28% |
| Microcrystalline wax | 8% |
| Carnauba wax | 8% |
| Trioleyl phosphate | 1% |
| 2-Oleoylamino-1,3-octadecanediol | 0.5% |

EXAMPLE 3

Moisturizing Cream for Delicate Lips

| | |
|---|---|
| Water | q.s. for 100% |
| α-Hydroxypalmitoyldihydrosphingosine | 0.2% |
| Methylparaben | 0.2% |
| Sorbitan tristearate | 1.4% |
| Cetyl alcohol | 5.5% |
| Glyceryl stearate | 4.8% |
| Polyethylene glycol (40 EO) stearate | 3% |
| Parleam oil | 23% |
| Potassium cetyl phosphate | 1% |
| Fragrance + dye | q.s. |

EXAMPLE 4

Comfort Balm

| | |
|---|---|
| $C_{24}$ Triglyceride | 10% |
| Dioctyldodecyl dimer dilinoleate | 24% |
| Octyldodecanol | 15% |
| Caprylic/capric acid triglyceride | 10% |
| Lanoline oil | 12% |
| Propoxylated lanolin | 6% |
| Acetylated lanolin | 6% |
| Polyethylene wax | 10% |
| Octaconasyl stearate | 5% |
| Zinc oxide | 0.5% |
| α-Hydroxypalmitoyldihydrosphingosine | 0.2% |
| Ascorbyl palmitate | 0.2% |
| Dye and fragrance | q.s. |

EXAMPLE 5

Stick for Repairing Sensitive Lips

| | |
|---|---|
| Hectorite modified by distearyldimethylammonium chloride | 0.5% |
| Liquid lanolin | 27.2% |
| Microcrystalline wax | 10.5% |
| Polyglycerolated (3 mol) beeswax | 4.2% |
| Acetylated lanolin | 6.7% |
| Arara oil (oleic acid esters) | 13.5% |
| Oxypropylenated (5 PO) lanolin wax | 6.7% |
| Oleyl erucate | 13.5% |
| Oleic/linoleic/linolenic acid triglycerides | 1.7% |
| Palmitic/oleic/linoleic acid triglycerides | 14.5% |
| Ascorbyl tetraisopalmitate | 1.0% |

EXAMPLE 6

Soothing Gloss

| | |
|---|---|
| Polybutene (Indopol H1500 ® from Amoco) | 43.9% |
| $C_{12}$-$C_{15}$ Alkyl benzoate (Finsolv TN ® from Finetex) | 33.0% |
| PVP/hexadecane copolymer | 22.0% |
| Octyldodecyl PCA (Ceramidone ® from Solabia) | 0.5% |
| α-Hydroxypalmitoylsphingosine | 0.1% |
| Vitamin C cetyl ether (Nikkol) | 0.5% |

EXAMPLE 7

Liquid Lipstick for Delicate Lips

| | |
|---|---|
| Aqueous polyurethane dispersion (Neorez R-981) | q.s. for 100.00% |
| Pigment | 1.00% |
| Plasticizing agent (glycerol) | 1.25% |
| Sodium PCA | 1.00% |
| Glycopyranosyl-L-ascorbic acid (Hayashibara) | 0.50% |

EXAMPLE 8

Soothing Stick

| | |
|---|---|
| Hectorite modified by distearyldimethylammonium chloride | 0.5% |
| Liquid lanolin | 26.2% |
| Microcrystalline wax | 10.5% |
| Polyglycerolated (3 mol) beeswax | 4.2% |
| Acetylated lanolin | 7.7% |
| Arara oil (oleic acid esters) | 13.5% |
| Oxypropylenated (5 PO) lanolin wax | 6.7% |
| Oleyl erucate | 13.5% |
| Palmitic/oleic/linoleic acid triglycerides | 15.2% |
| Lauryl PCA | 1.0% |
| Ascorbyl tetraisopalmitate | 1.0% |

Although the present invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method for the cosmetic treatment of a subject having delicate lips, the method comprising:
applying to the lips of said subject a composition comprising a ceramide precursor comprising a 6-hydroxy-4-sphingenine base.

2. The method according to claim 1, wherein the ceramide precursor comprising a 6-hydroxy-4-sphingenine base is a compound defined by formula (I):

$$R_1\text{—CHOH—CH(NH—COR}_2\text{)(CH}_2\text{OH)} \qquad (I)$$

in which:
$R_1$ represents a $C_3$ to $C_{30}$ alkyl or alkenyl radical, and
$R_2$ represents a hydrogen atom or a $C_3$ to $C_{30}$ hydrocarbon radical which is linear and optionally hydroxylated, the hydroxyl group being in the α position with respect to the carbonyl group.

3. The method according to claim 2, wherein $R_1$ represents a $C_{14}$ to $C_{18}$ alkyl or alkenyl radical.

4. The method according to claim 3, wherein $R_2$ represents a $C_{11}$ to $C_{19}$ hydrocarbon radical.

5. The method according to claim 3, wherein the compound of formula (I) is selected from N-oleoyldihydrosphingosine and ceramides V.

6. The method according to claim 2, wherein the ceramide precursor comprising a 6-hydroxy-4-sphingenine base is a ceramide V or a ceramide V derivative.

7. The method according to claim 5, wherein the ceramide V is a compound of formula (IV) or (V):

(IV)

(V)

in which n is from 1 to 28.

8. The method according to claim 1, wherein the composition further comprises at least one additional active principle chosen from another protective agent for delicate lips, moisturizing agents, desquamating agents, agents for combating pollution or free radicals, soothing agents, and healing agents.

9. The method according to claim 1, wherein the composition further comprises at least one additional active principle chosen from Centella asiatica extracts, madecassoside, vitamin B5, hydroxyethylurea, zinc oxide, and C-β-D-xylopyranoside-2-hydroxypropane.

10. The method according to claim 9, wherein the composition further comprises:
ascorbic acid or an ascorbic acid analogue, and
a natural moisturizing factor deriving from the decomposition of filaggrin.

11. The method according to claim 10, wherein the ascorbic acid analogues are selected from the group consisting of ascorbic acid salts, ascorbic acid esters, ascorbic acid sugars, and the derivatives of formula (II):

in which:
$R_6$ represents a hydrogen atom, a hydrocarbon chain having from 15 to 20 carbon atoms, a sugar residue, a carbonyl group, an alkyloxycarbonyl group or a carbamoyl group, or $R_6O$ represents a sulphate functional group or a phosphate functional group,
$R_7$ represents a hydrogen atom, a sugar residue or a —$COR_{10}$ group where $R_{10}$ is chosen from:
  (a) a saturated or unsaturated, linear, cyclic or branched, $C_1$-$C_{20}$ hydrocarbon radical which is optionally hydroxylated,
  (b) an optionally hydroxylated aryl radical, and
  (c) an aralkyl radical of formula (III):

where R, R' and R", which are identical or different, represent a hydrogen atom or a hydroxyl, alkoxy, fluoroalkoxy or alkylcarbonyloxy radical, and
$R_8$ and $R_9$, which are identical or different, represent a hydrogen atom or a —$COR_{10}$ group as defined above or, taken together, form an isopropylidene radical, or a salt of this derivative.

12. The method according to claim 11, wherein the ascorbic acid analogues are selected from the group consisting of ascorbyl palmitate, magnesium ascorbyl-2-phosphate, glucopyranosyl-L-ascorbic acid, sodium ascorbate, sodium L-ascorbyl-2-phosphate, ascorbyl tetraisopalmitate, and vitamin C cetyl ether.

13. A method for the cosmetic treatment of a subject having delicate lips, the method comprising:
applying to the lips of said subject a composition comprising a ceramide precursor comprising a 6-hydroxy-4-sphingenine base, and
ascorbic acid or an ascorbic acid analogue.

14. The method according to claim 1, wherein the composition is provided in the form of a paste, a solid, a cream, a foam, a spray, a powder, or of a liquid.

15. The method according to claim 1, wherein the composition is provided in the form of an oil-in-water (O/W), oil-in-polyol, water-in-oil (W/O) or water-in-polyol emulsion, of a multiple (W/O/W or polyol/O/W or O/W/O) emulsion, of an anhydrous gel, of a soft paste or solid, of a liquid oily phase, of a suspension, of a dispersion, or of a solution.

16. The method according to claim 1, wherein the composition is provided in the form of an anhydrous solid composition.

17. The method according to claim 1, wherein the composition comprises the ceramide precursor comprising a 6-hydroxy-4-sphingenine base in a content ranging from 0.0001 to 10% by weight with respect to the total weight of the composition.

18. The method according to claim 1, wherein the composition further comprises ascorbic acid or an ascorbic acid analogue in a content ranging from 0.0001 to 20% by weight with respect to the total weight of the composition.

19. The method according to claim 1, wherein the composition is provided in the form of a dermatological composition or care composition for the lips, in the form of a composition for the antisun protection of the lips, in the form of a care base for delicate lips, in the form of a lip balm or in the form of a coloured product for making up the lips.

20. The method according to claim 1, wherein the composition is thickened with at least one thickening agent chosen from fatty-phase gelling agents, waxes, pasty fatty substances, fillers, and their mixtures.

21. The method according to claim 1, wherein the composition further comprises at least one colouring material selected from the group consisting of dyes, pigments, pearlescent agents, and their mixtures.

22. The method according to claim 10, wherein the natural moisturizing factor deriving from the decomposition of filaggrin is selected from the group consisting of serine, tryptophan, pyrrolidone carboxylic acid, uronic acid, their corresponding salts, and derivatives thereof.

23. The method according to claim 1, wherein the composition further comprises one or more additional active principles in a total content ranging from 0.001 to 30% by weight with respect to the total weight of the composition.

24. The method according to claim 23, wherein the composition further comprises ascorbic acid or an ascorbic acid analogue.

25. The method according to claim 1, wherein:
the subject is affected by scales and/or dry plaques associated with or not associated with feelings of discomfort and/or tightness and/or smarting or are predisposed to exhibit these sensations; and
the ceramide precursor comprising a 6-hydroxy-4-sphingenine base is defined by formula (I):

$$R_1—CHOH—CH(NH—COR_2)(CH_2OH) \quad (I)$$

where:
$R_1$ represents a $C_3$ to $C_{30}$ alkyl or alkenyl radical; and
$R_2$ represents a hydrogen atom or a $C_3$ to $C_{30}$ hydrocarbon radical that is linear and optionally hydroxylated, the hydroxyl group being in the α position with respect to the carbonyl group.

26. A method for the cosmetic treatment of a subject whose lips are affected by chapping and/or cracks and/or bleeding associated with or not associated with scales and/or dry plaques and/or feeling of discomfort and/or tightness and/or smarting or are predisposed to exhibit these disorders, the method comprising:
applying, to the lips of said subject, a composition comprising a ceramide precursor comprising a 6-hydroxy-4-sphingenine base defined by formula (I):

$$R_1—CHOH—CH(NH—COR_2)(CH_2OH) \quad (I)$$

where:
R$_1$ represents a C$_3$ to C$_{30}$ alkyl or alkenyl radical; and
R$_2$ represents a hydrogen atom or a C$_3$ to C$_{30}$ hydrocarbon radical that is linear and optionally hydroxylated, the hydroxyl group being in the α position with respect to the carbonyl group.

27. The method according to claim 1, wherein the composition is applied to a vermilion border of the lips.

28. The method according to claim 13, wherein the composition is applied to a vermilion border of the lips.

29. The method according to claim 26, wherein the composition is applied to a vermilion border of the lips.

* * * * *